United States Patent
Sysun et al.

(10) Patent No.: US 11,612,355 B2
(45) Date of Patent: Mar. 28, 2023

(54) INFLATABLE VEST FOR RESPIRATORY ASSESSMENT

(71) Applicant: Fresenius Medical Care Holdings, Inc., Waltham, MA (US)

(72) Inventors: Lisa Sysun, Chelmsford, MA (US); Daniel L. Sloat, Wakefield, MA (US)

(73) Assignee: FRESENIUS MEDICAL CARE HOLDINGS, INC., Waltham, MA (US)

(*) Notice: Subject to any disclaimer, the term of this patent is extended or adjusted under 35 U.S.C. 154(b) by 225 days.

(21) Appl. No.: 16/953,810

(22) Filed: Nov. 20, 2020

(65) Prior Publication Data

US 2022/0160300 A1    May 26, 2022

(51) Int. Cl.
| | |
|---|---|
| A61B 5/00 | (2006.01) |
| A61B 7/00 | (2006.01) |
| A61B 5/08 | (2006.01) |
| A61B 7/04 | (2006.01) |
| A61B 5/024 | (2006.01) |
| A61B 5/145 | (2006.01) |

(52) U.S. Cl.
CPC .......... *A61B 5/6805* (2013.01); *A61B 5/0004* (2013.01); *A61B 5/0015* (2013.01); *A61B 5/024* (2013.01); *A61B 5/08* (2013.01); *A61B 5/14542* (2013.01); *A61B 7/003* (2013.01); *A61B 7/04* (2013.01)

(58) Field of Classification Search
CPC ... A61B 5/6804–6805; A61B 7/04–045; Y10S 2/03
See application file for complete search history.

(56) References Cited

U.S. PATENT DOCUMENTS

| | | | |
|---|---|---|---|
| 5,252,787 | A | 10/1993 | Moore et al. |
| 5,288,286 | A * | 2/1994 | Davis ............... A61F 5/0111 602/5 |
| 7,976,480 | B2 | 7/2011 | Grajales et al. |
| 8,193,465 | B2 | 6/2012 | Yang et al. |
| 8,419,652 | B2 | 4/2013 | Rajamani et al. |
| 9,008,794 | B2 | 4/2015 | Alexandre |

(Continued)

FOREIGN PATENT DOCUMENTS

| | | | |
|---|---|---|---|
| JP | 2004181025 A | * | 7/2004 |
| WO | 2014/097297 A1 | | 6/2014 |
| WO | 2015/138515 A1 | | 9/2015 |

OTHER PUBLICATIONS

Bhaskar, Anand. "A simple electronic stethoscope for recording and playback of heart sounds." Adv Physiol Educ. Dec. 2012;36(4):360-2. (Year: 2012).*

(Continued)

*Primary Examiner* — Meredith Weare
(74) *Attorney, Agent, or Firm* — Kilyk & Bowersox, P.L.L.C.

(57) ABSTRACT

A lightweight inflatable vest is provided with embedded listening devices. Once inflated, the vest enables a physician to hear amplified lung sounds and heart beats and rhythms of a patient wearing the vest, via connection to a smart phone application, through a patient portal, or the like. By using the device on a patient, a physician is provided with an accurate way to perform a respiratory and heart health assessment of the patient during a telehealth visit.

15 Claims, 10 Drawing Sheets

(56) References Cited

U.S. PATENT DOCUMENTS

| | | | |
|---|---|---|---|
| 2011/0009759 A1* | 1/2011 | Rajamani | A61B 5/6805 |
| | | | 600/526 |
| 2013/0066217 A1* | 3/2013 | Matsunami | A61B 5/02141 |
| | | | 600/499 |
| 2014/0100469 A1* | 4/2014 | Sagalovich | A61B 7/04 |
| | | | 600/300 |
| 2019/0231262 A1* | 8/2019 | Nasry | A61B 7/026 |
| 2019/0298269 A1* | 10/2019 | Atashbar | A61B 5/002 |
| 2021/0059605 A1* | 3/2021 | Myers | A61B 5/27 |

OTHER PUBLICATIONS

Form PCT/ISA/237, Written Opinion of the International Searching Authority for PCT Application No. PCT/US2021/056740, dated Feb. 21, 2022.
Form PCT/ISA/210, International Search Report for PCT Application No. PCT/US2021/056740, dated Feb. 21, 2022.
Huitaek Yun et al., "Development of internal sound sensor using stethoscope and its applications for machine monitoring", 48th SME North American Manufacturing Research Conference, NAMRC 48, ScienceDirect, Procedia Manufacturing 48 (2020) pp. 1072-1078.

\* cited by examiner

INFLATABLE VEST FOR RESPIRATORY ASSESSMENT

FIELD OF THE INVENTION

The present invention relates to telehealth doctor appointments and respiratory assessments.

BACKGROUND OF THE INVENTION

It is challenging for a physician to perform an accurate respiratory assessment on a patient during a Telehealth visit. Accurate assessments are best done in-person so that the physician, while wearing a conventional stethoscope, can listen to a patient's breathing and heart. A need exists for a device and system that enables physicians to listen to a home patient's lung sounds and heart. A need also exists for a device, system, and method to enable a physician, nurse, or clinician, to accurately conduct a respiratory assessment via a smart phone application or through a portal.

SUMMARY OF THE INVENTION

It is an objective of the present invention to provide physicians with an accurate way to perform a respiratory assessment on home patients during an online Telehealth visit.

It is an objective of the present invention to provide a respiratory assessment device and system that are easy for both home patients and physicians to use, and that use low-cost components that are easy to manufacture.

It is an objective of the present invention to provide a system and pathway that enable data conversion to complimentary digital solutions, and uploading through a PatientHub application a smartphone application, or the like.

According to the present invention, an inflatable vest is provided that comprises one or more stethoscope listening devices, for example, in a back (posterior) panel of the vest, connected by tubing, to an output port. The output port can be a physical property output port, an electronic information output port, or a combination thereof. The number of listening devices and their positions can vary. Tubing near the stethoscope device or devices can contain small microphones to amplify sound to conductor relays. The relays can connect to a USB port in the vest, for example, in the side, front, or bottom of the vest. A patient can use a USB cord to connect the vest to a mobile device, laptop, or other computer or processor. Wireless signal transmission can also be used.

BRIEF DESCRIPTION OF THE DRAWINGS

The invention may be more fully understood with reference to the accompanying drawings. The drawings are intended to illustrate, not limit, the present teachings.

DETAILED DESCRIPTION OF THE INVENTION

Figure 1:
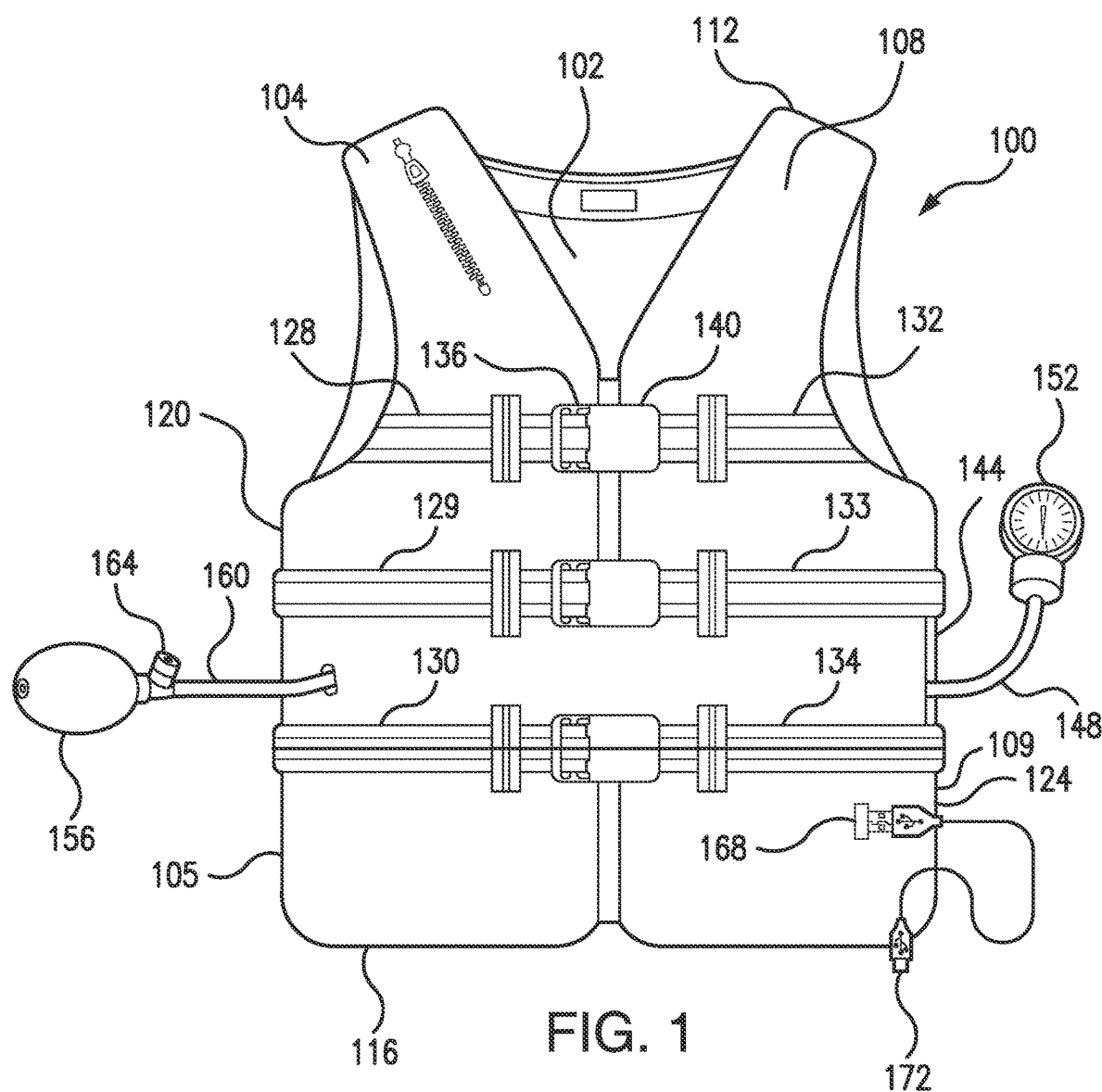
FIG. 1 is a front view of an inflatable vest according to an embodiment of the present invention, in a closed configuration.

According to various embodiments, the present invention provides an inflatable vest for respiratory assessment. The vest can be useful for many applications, including, for example, a telehealth appointment. The inflatable vest can comprise a vest garment configured to be worn on a torso of a patient. The vest garment comprising a garment front, a garment back, and an inflatable bladder. The inflatable bladder can be incorporated in or on at least the garment back. The garment back can include an inside surface configured to press against the back of a patient and at least one stethoscope recess recessed into the inside surface. The inflatable vest can comprise at least one stethoscope. The stethoscope, or each stethoscope, can comprise a bell, a diaphragm across the bell, and a pressure tube extending away from the bell. One or more, and all or some, of the one or more stethoscopes can be sized such that the bell fits within one respective stethoscope recess of the at least one stethoscope recess. The fit can be such that the diaphragm is flush with the inside surface of the garment back. At least one microphone is provided, positioned within at least one pressure tube of at least one of the stethoscopes. The inflatable vest is configured such that, when the at least one stethoscope is recessed into the at least one stethoscope recess, the inflatable vest is worn by a patient, and the inflatable bladder is inflated, the diaphragm of the at least one stethoscope is pressed against the back of the patient.

The inflatable vest can be modular such that at least one stethoscope is removably attached to the vest garment. For example, the inflatable vest can comprise an outer shell having an inside surface, an inflatable liner, and a coupler. The inflatable liner can define an inflatable bladder and have an outside surface and an inside surface. The inside surface of the inflatable liner can define at least one stethoscope recess. The outside surface of the inflatable liner can be removably attached to the inside surface of the outer shell, by the coupler. The coupler can comprise, for example, a zipper, buttons, hook and loop fasteners, buckles, ties, snaps, clips, magnetic buttons, clasps, pressure sensitive adhesives, laces, combinations thereof, and the like.

The stethoscope can be part of a matrix of stethoscopes. The matrix of stethoscopes can be releasably attached to the inside surface of the inflatable liner. The inside surface of the inflatable liner can comprise a plurality of stethoscope recesses comprising a plurality of stethoscope bell recesses and a plurality of stethoscope pressure tube channels. The stethoscope matrix can further comprise an electronic output port connected to the matrix of stethoscopes. The electronic output port can comprise a cable port, a wireless transmitter, or a combination thereof, and can be configured to transmit data captured by the microphone, to a computing system, a recording system, a combination thereof, or the like. The inside surface of the inflatable liner can further comprise an electronic output port recess that receives and retains the electronic output port therein.

Each of the plurality of bell recesses can comprise an inner wall defining a bell shape, and a lip radially extending inwardly from a periphery of the inner wall. The lip can comprise an elastically deformable material. Each of the pressure tube channels can comprise an inner wall defining a tubular shape having an opening along a length thereof. The opening can be configured to receive a respective pressure tube in the channel. The inner wall can comprise an elastically deformable material. The opening can have a width that is less than a diameter of the pressure tube.

The coupler can comprise a first pair of zipper halves attached to the inside surface of the outer shell, and a second pair of zipper halves attached to the outside surface of the inflatable liner. The first pair of zipper halves can be zipped to the second pair of zipper halves. The coupler can comprise one or more of hook patches and loop patches attached to the outside surface of the inflatable liner, and one or more of hook patches and loop patches attached to the inside surface of the outer shell. The inflatable liner can comprise an inflation port connected to the inflatable bladder, and a pressure port connected to the inflatable bladder. The inflatable vest can further comprise a vest inflation bulb that includes a bulb coupler. The bulb coupler can be releasably attached to the inflation port. The inflatable vest can further comprise an aneroid manometer gauge comprising a gauge coupler. The gauge coupler can be releasably attached to the pressure port.

According to various embodiments of the present invention, a method of assembling a modular inflatable vest as described herein, is provided. The method can comprise coupling the inflatable liner to the outer shell, using the coupler. The method can comprise positioning the at least one stethoscope in the at least one stethoscope recess. The method can comprise inflating an inflatable liner. The method can comprise sending signals representative of respiratory assessments, from the inflatable vest, to a remote location.

The present invention also provides a method of making a respiratory assessment of a patient. The method can comprise placing the inflatable vest on a patient and inflating the inflatable bladder to press the at least one stethoscope against the back of the patient. The method can comprise transmitting respiratory signals generated by the at least one stethoscope, from the inflatable vest, to a receiver that is remote from the inflatable vest. The inflatable vest can further comprise a heart rate monitor and a pulse oximeter. The method can further comprise transmitting heart rate signals and blood oxygen signals from the inflatable vest to a receiver that is remote from the inflatable vest.

With reference now to the drawings, FIG. 1 shows an inflatable vest 100 according to an embodiment of the present invention. Inflatable vest 100 comprises a back panel 102, a right front panel 104, and a left front panel 108. Right front panel 104 terminates at a crease 105 and left front panel 108 terminates at a crease 100. Inflatable vest 100 has a vest top 112, a vest bottom 116, a right side 120, a left side 124, three right straps 128, 129, and 130, and three left straps 132, 133, and 134. Each of three right straps 128, 129, and 130, terminates at a respective buckle receiver. The buckle receiver of right strap 128 is shown at reference numeral 136. Each of three left straps 132, 133, and 134 terminates at a respective buckle. The buckle for left strap 132 is shown at reference numeral 140. Although straps and buckles are depicted, other vest fasteners can be used, for example, a zipper, buttons, hook and loop fasteners, combination thereof, and the like.

Along left side 124 is a side pocket 144 into which a pressure tube 148 for an aneroid manometer gauge 152, extends. A vest inflation bulb 156 can be squeezed to pump air through a pressure tube 160 to inflate the vest, for example, to inflate one or more inflatable bladders inside back panel 102, right front panel 104, a left front panel 108, or a combination thereof. An air release valve 164 is provided along pressure tube 160 so that inflatable vest 100 can be deflated, for example, when not in use, when being stored, or when a patient is putting on the inflatable vest.

An output port 168 is provided and enables electrical connection and/or data transfer communication of inflatable vest 100 to a signal-sending device, for example, a cell phone, a mobile device, a laptop computer, a desktop computer, a smart watch, a tablet, a router, a modem, a hub, a smart speaker, or the like. A USB cable 172 or other suitable cable can be provided for such a purpose.

Figure 2:
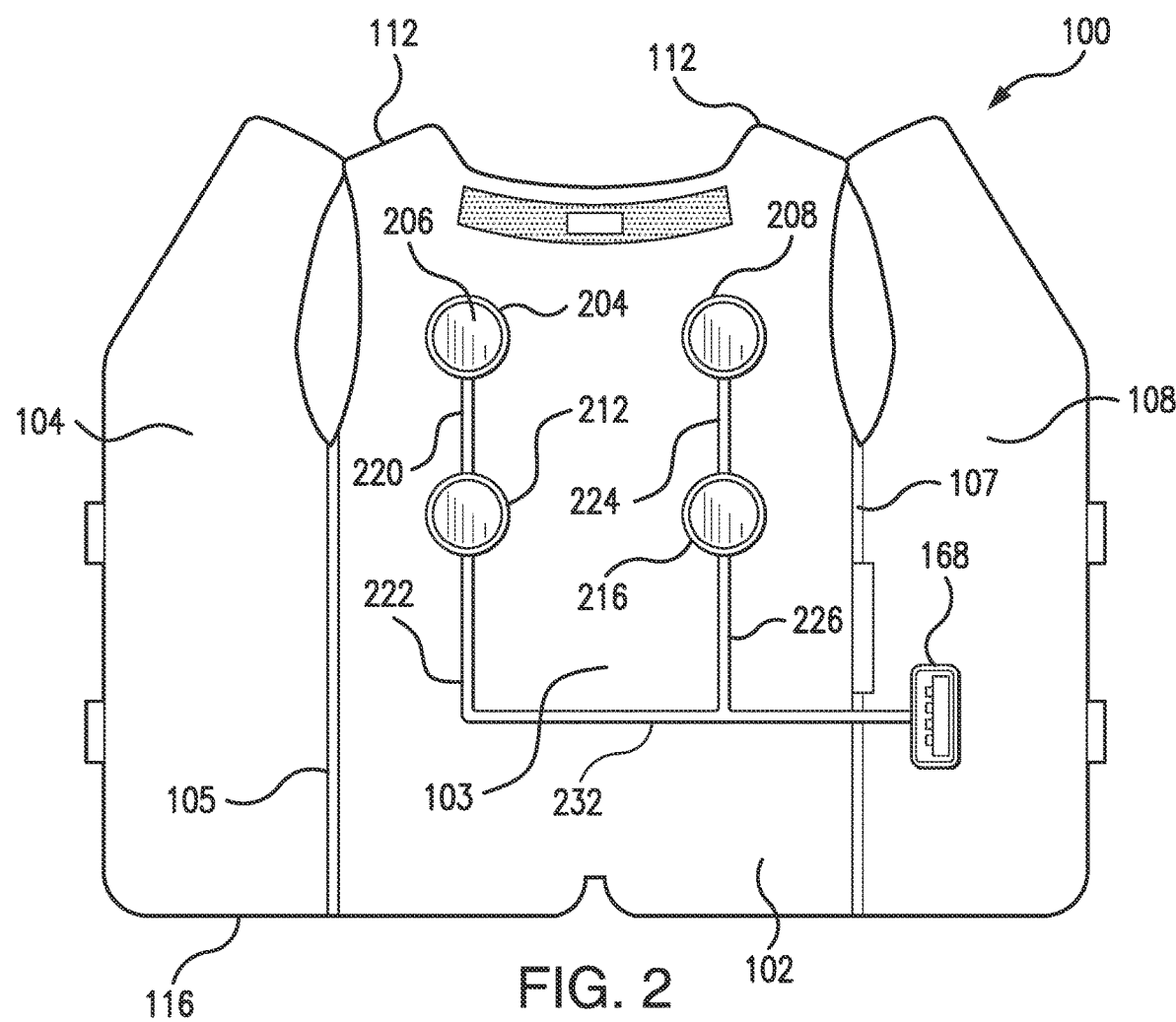
FIG. 2 is a front view of the inflatable vest shown in FIG. 1, in an open configuration.
Figure 3:
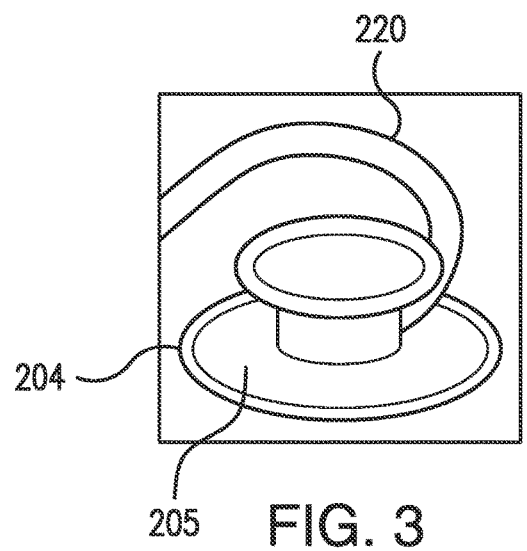
FIG. 3 is a close-up view of an amplified stethoscope that can be used as part of the inflatable vest shown in FIGS. 1 and 2.

As shown in FIGS. 2 and 3, A first stethoscope 204 having a listening cup 205 is mounted on an inner surface 103 of back panel 102 such that a flat listening bell surface 206 of first stethoscope 204 is exposed, for example, flush with inner surface 103. A pneumatic pressure tube 220 extends from first stethoscope 204, inside back panel 102, to propagate sound waves and pressure waves from first stethoscope 204 toward a microphone (FIG. 4) within pressure tube 220. An electrical signal from the microphone is communicated via wires, one or more of which may or may not be shielded, to output port 168. A second stethoscope 208, a third stethoscope 212, and a fourth stethoscope 216 can also be similarly mounted in inflatable vest 100, for example, also in back panel 102. Each of stethoscopes 208, 212, and 216 includes a flat listening bell surface 210, 214, 218, respectively. Stethoscopes 208, 212, and 216 can be mounted in back panel 102 such that flat listening bell surfaces 210, 214, and 218 can be exposed, and flush with inner surface 103 of back panel 102. Similar to the connections and microphone for first stethoscope 204, each of stethoscopes 208, 212, and 216 can be connected to output port 168 via, for example, a pneumatic tube, a pressure tube, a plastic tube, one or more wires, a shielded wire, a conduit, a combination thereof, or the like. As shown in FIG. 2, each of stethoscopes 208, 212, and 216 is connected to output port 168 via a respective connector, for example, pneumatic pressure tubes 222, 224, and 226 as shown. As described in more detail below, a respective microphone and corresponding wiring is provided in each of pneumatic pressure tubes 222, 224, and 226.

Connectors 220, 222, 224, and 226 do not necessarily have to be pressure tubes or any other type of conduit, but can instead simply comprise wires leading from each of stethoscopes 204, 208, 212, and 216 to output port 168. In this regard, microphones can be included inside each of stethoscopes 204, 208, 212, and 216 such that only electrical wiring to send microphone signals from the stethoscopes to output port 168, is provided.

According to an embodiment of the present invention, sound waves, pressure pulses, electrical signals, combinations thereof, and the like, collectively, "signals," can be sent along connectors 220, 222, 224, and 226. Signals sent along one or more of connectors 220, 222, 224, and 226 can merge with signals sent along one or more of the other connectors. Thus, sound signals picked up by the respective microphones can be combined to form a single composite signal. For example, microphone signals emitted by or resulting from first stethoscope 204 can be combined or merged with microphone signals emitted by or resulting from third stethoscope 212, to form a combined signal, and the combined signal can be transmitted along a common connector 232 to output port 168. Similarly, signals from second stethoscope 208 can travel along connector 224 and can merge with signals from fourth stethoscope 216, travelling along connector 228, or can independently be transferred to output port 168.

According to various embodiments, respective signals sent along each of connectors 220, 222, 224, and 226 can be maintained as separate signals that can be received at and transferred from output port 168. If kept separate, a physician, nurse, or clinician, herein, a "diagnostician," can independently hone into the microphone signal generated by just one of the four different stethoscopes. For example, signals from first stethoscope 204 and third stethoscope 212 can independently travel to output port 168 without merging or combining. Signals travelling along connectors 220, 222, 224, and 226 can merge or commonly travel along a manifold tube 232 that in turn reports to or provides signals to output port 168. By maintaining the microphone signals separately, a diagnostician can hone in on just the sound of a patient's left lung, just the sound of a patient's right lung, just the sound of the top of a patient's left lung, just the sound of the bottom of a patient's left lung, just the sound of the top of a patient's right lung, or just the sound of the bottom of a patient's right lung.

Output port 168 can comprise wireless output signal-sending hardware, firmware, software, a combination thereof, or the like. Output port 168 can comprise an Ethernet port, a USB port, a co-axial port, a fire-wire port, or any other wired connection jack. Outport port 168 can comprise or be part of an integrated circuit that can include, for example, a signal processor, a signal amplifier, a noise gate, a signal compressor, a signal filter, a combination thereof, or the like.

FIGS. 4A-7 illustrate an embodiment of the present invention, which includes a modular inflatable vest with separable components. The modular inflatable vest includes an outer shell 400, an inflatable liner 500, and a stethoscope matrix 600. The present invention can further include a plurality of additional components that are attachable to the modular inflatable vest. The modular inflatable vest with separable components allows the inflatable vest to be disassembled, modified, reused in-part or in-whole, packaged, and easily cleaned.

Figure 4A:
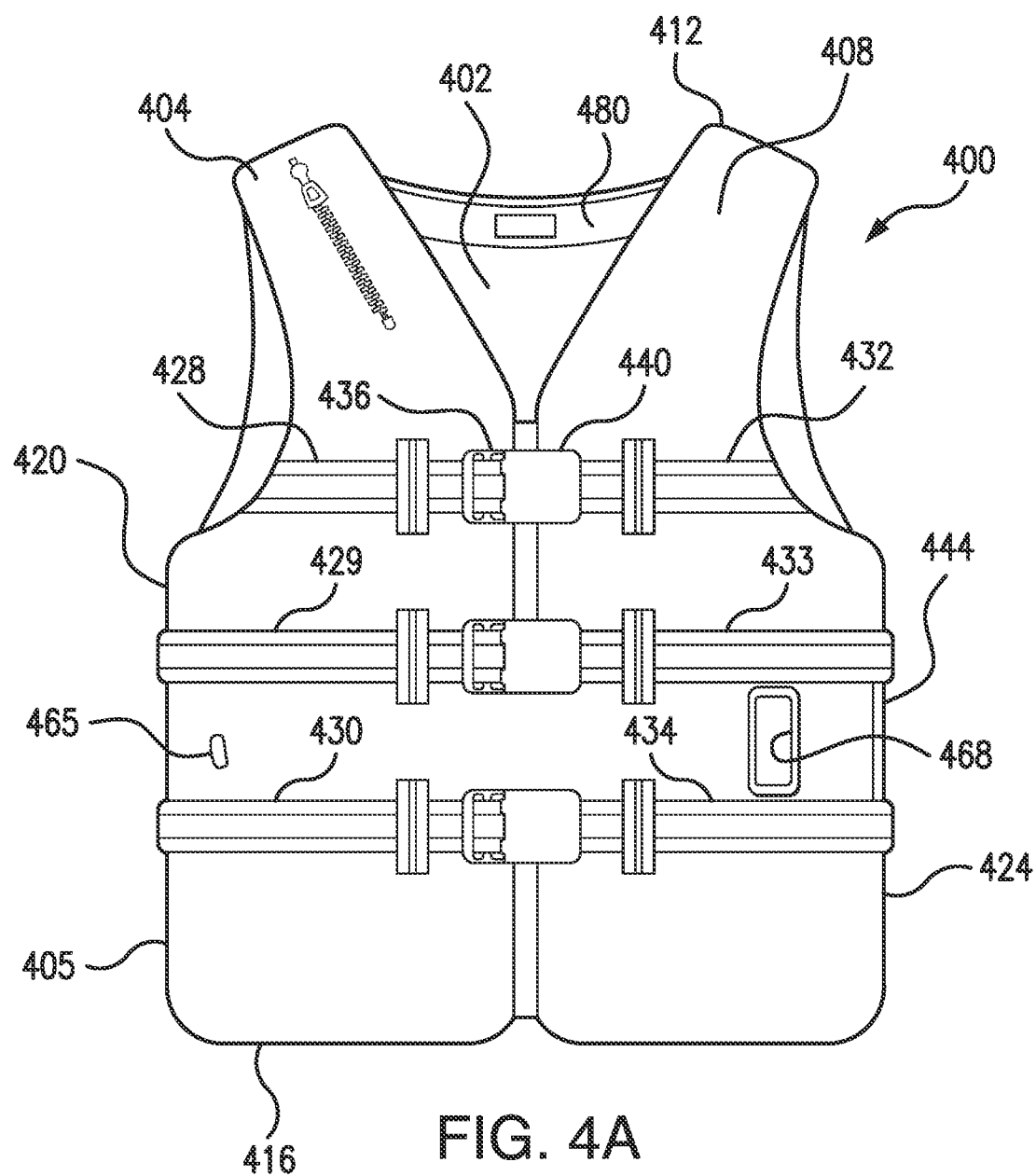
FIG. 4A is a front view of an outer shell, of a modular inflatable vest, in a closed configuration, according to various embodiments of the present invention.
Figure 4B:
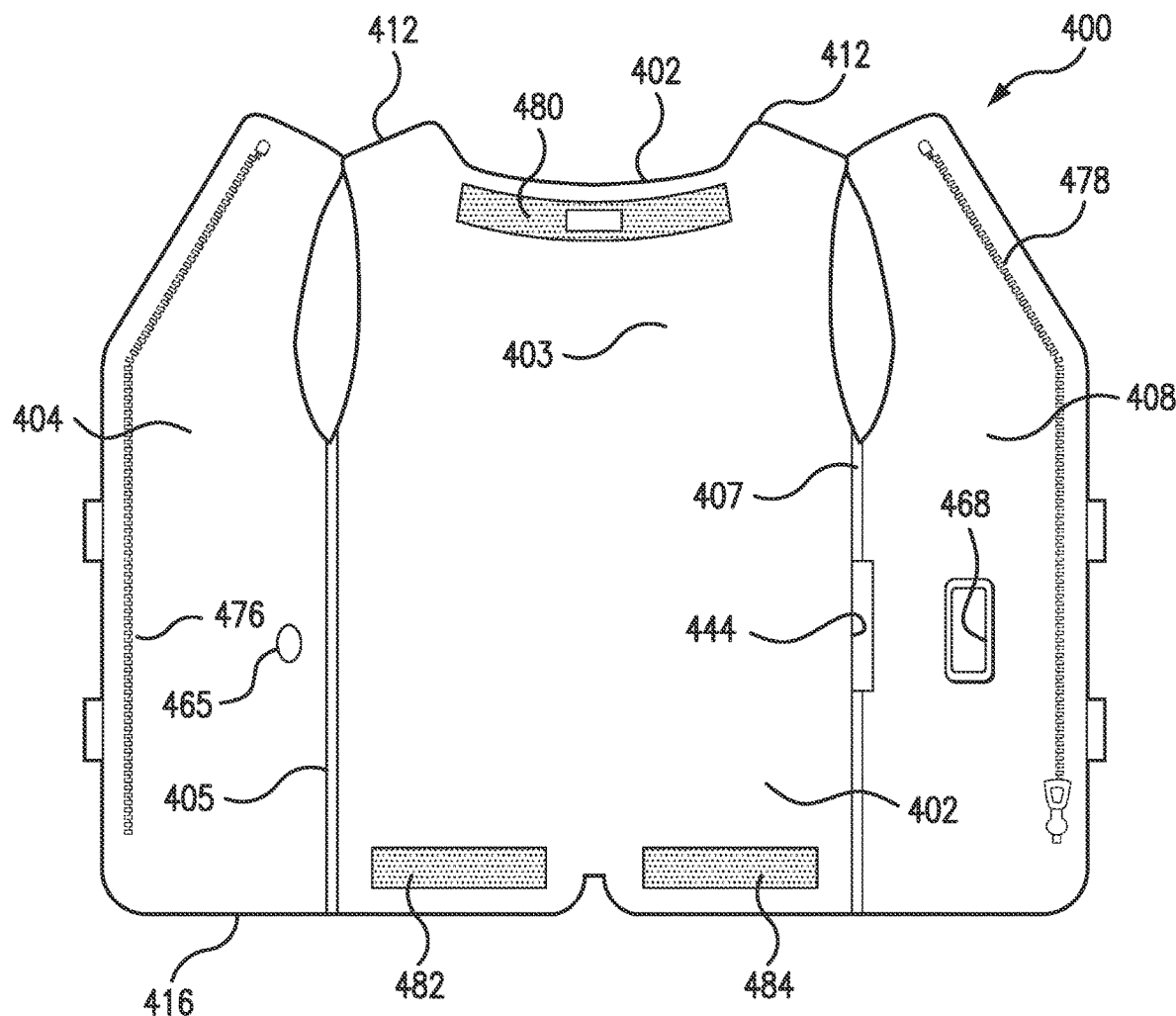
FIG. 4B is a front view of the outer shell shown in FIG. 4A, in an opened configuration.

FIGS. 4A and 4B illustrate outer shell 400. Outer shell 400 comprises a back panel 402, a right front panel 404, and a left front panel 408. Right front panel 404 terminates at a crease 405 and left front panel 408 terminates at a crease 407. Outer shell 400 has a top 412, a bottom 416, a right side 420, a left side 424, three right straps 428, 429, and 430, and three left straps 432, 433, and 434. Each of three right straps 428, 429, and 430 terminate at a respective buckle receiver. The buckle receiver of right strap 428 is shown at reference numeral 436. Each of three left straps 432, 433, and 434 terminate at a respective buckle. The buckle for left strap 432 is shown at reference numeral 440. Along left side 424 is a first opening 444 to provide clearance for connecting a pressure tube for an aneroid manometer gauge to the inflatable liner. A second opening 468 is defined through left front panel 408 to provide clearance for connecting a cable to an output port of the stethoscope matrix. A third opening 465 is defined through right front panel 404 to provide clearance for connecting a vest inflation bulb to the inflatable liner.

FIG. 4B illustrates outer shell 400 with buckle receivers and buckles detached and in an open position, showing an inside surface 403 of back panel 402, an inside surface of right front panel 404, and an inside surface of left front panel 408. Inside surface 403, and the inside surfaces of right front panel 404 and left front panel 408, can include a plurality of couplers that releasably connect with couplers of the inflatable liner to releasably retain the inflatable liner to inside surface 403 and the inside surfaces of right front panel 404 and left front panel 408 of outer shell 400. As shown in FIG. 4B, a first lower hook patch 482 and a second lower hook patch 484 can be stitched to inside surface 403 of back panel 402 adjacent to and above bottom 416. An upper hook patch 480 can be stitched to inside surface 403 of back panel 402 adjacent to and below top 412. The couplers can further include a first pair of zipper halves 476, 478. For example, a right shell zipper half 476 can be stitched to the inside surface along a substantial height of right front panel 404 and a left shell zipper half 478 can be stitched to the inside surface along a substantial height of left front panel 408. First lower hook patch 482, second lower hook patch 484, and upper hook patch 480 releasably connect to respective loop patches of the inflatable liner.

Likewise, right shell zipper half 476 and left shell zipper half 478 zip to respective zipper halves of the inflatable liner, thereby releasably attaching or coupling the inflatable liner to outer shell 400. Although hook and loop fasteners and zippers are depicted in particular locations, the same or other fasteners can be used in other locations. Other fasteners can include, but are not limited to, buttons, buckles, ties, snaps, clips, magnetic buttons, clasps, pressure sensitive adhesives, laces, a combination thereof, and the like.

Figure 5A:
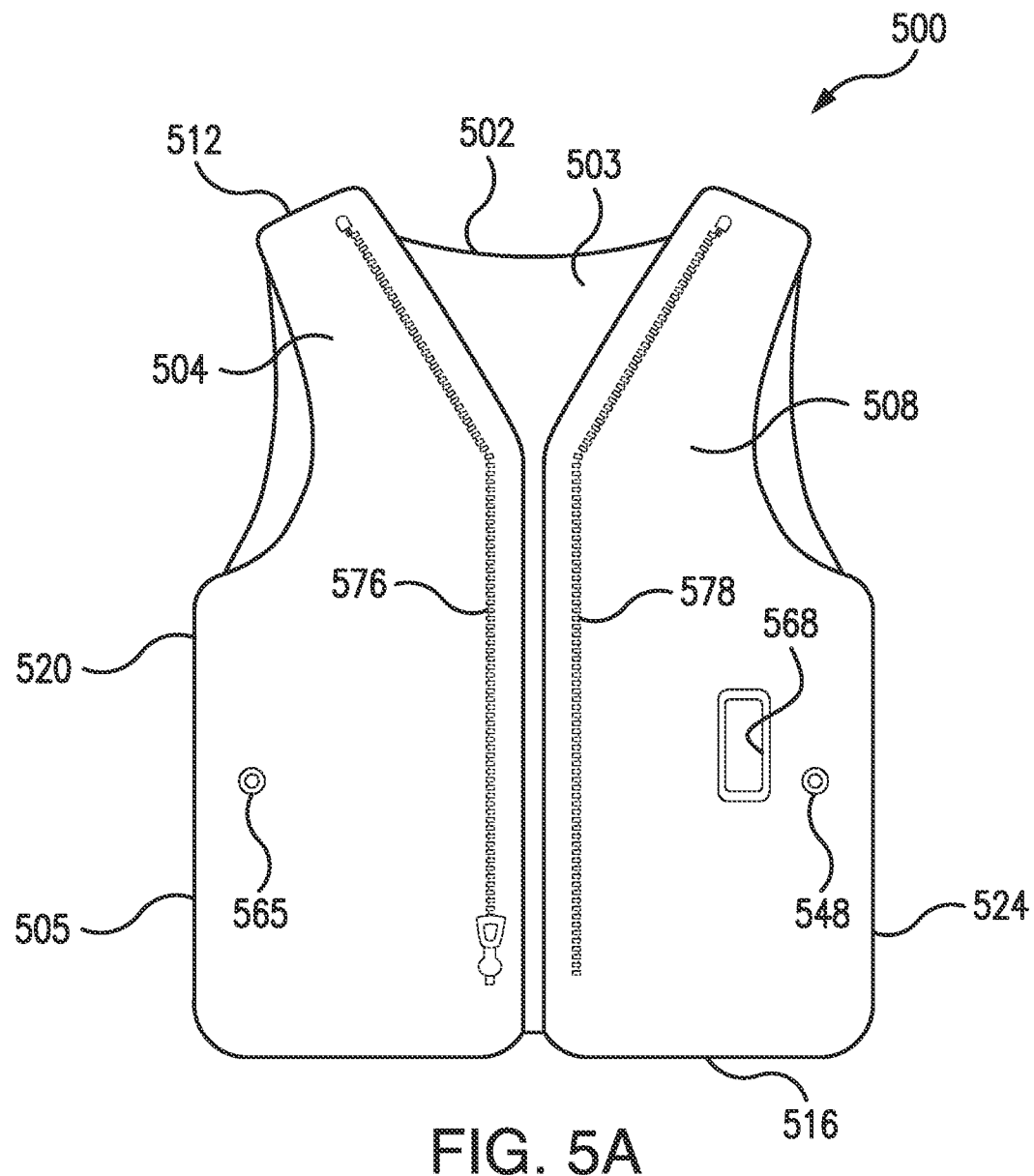
FIG. 5A is a front view of an inflatable liner in a closed configuration, which can be used with the outer shell shown in FIGS. 4A and 4B, according to various embodiments of the present invention.
Figure 5B:
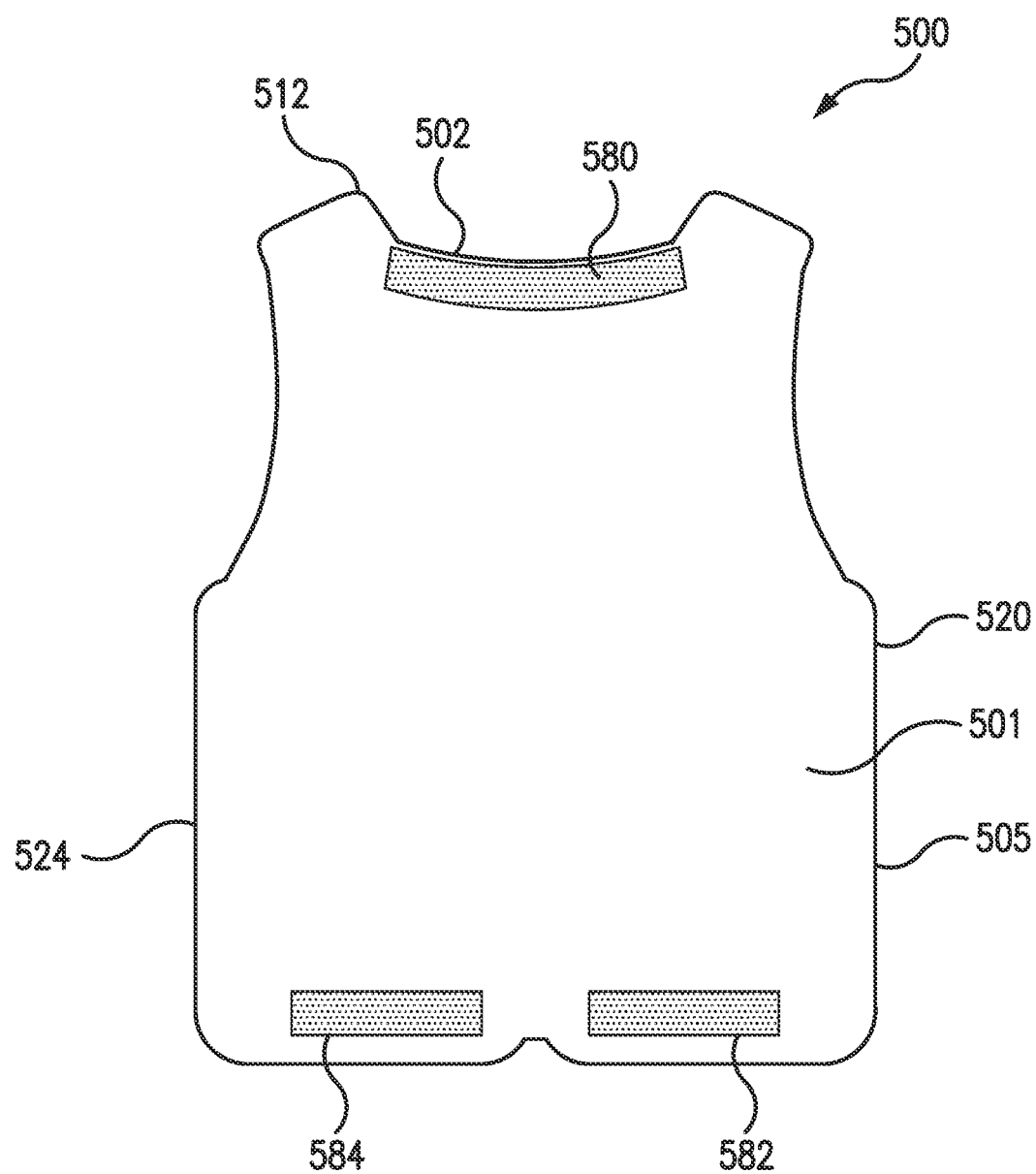
FIG. 5B is a back view of the inflatable liner shown in FIG. 5A, in the closed configuration.
Figure 5C:
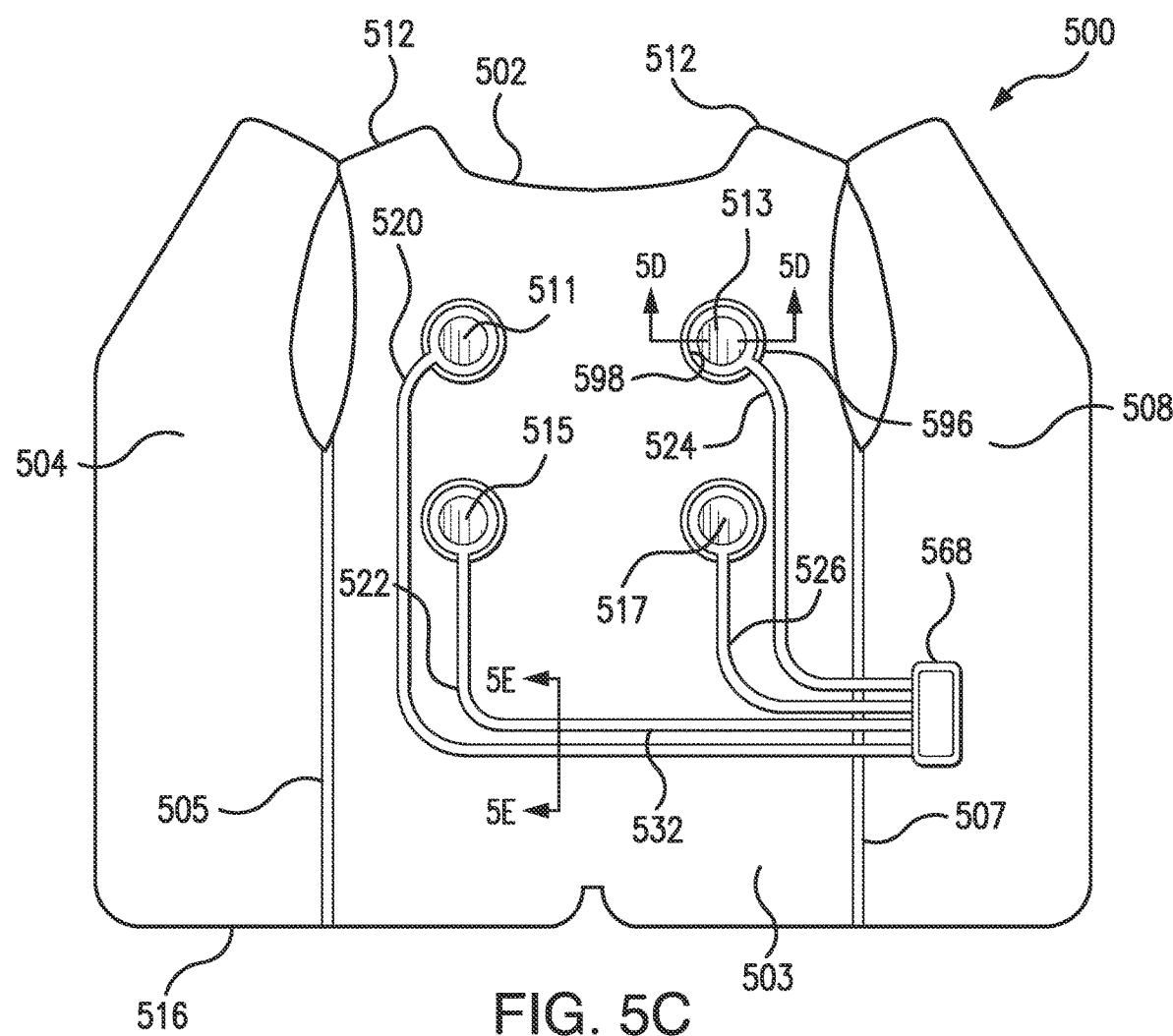
FIG. 5C is a front view of the inflatable liner shown in FIG. 5A, in an opened configuration, showing stethoscope recesses and pressure tube channels for housing a stethoscope assembly or matrix according to various embodiments of the present invention.

FIGS. 5A-5C illustrate inflatable liner 500. Inflatable liner 500 comprises a back panel 502, a right front panel 504, and a left front panel 508. Right front panel 504 terminates at a crease 505 and left front panel 508 terminates at a crease 507. Inflatable liner 500 has a top 512, a bottom 516, a right side 520, and a left side 524. A first port 565 is on right front panel 504. First port 565 can include a valve that opens to an inflatable bladder. Inflatable liner 500 can have an inner wall, an outer wall, and an inflatable space between the walls, defining an inflatable bladder. As such, inflatable liner 500 can be said to have an inflatable bladder.

The valve of first port 565 can open when a coupler of a vest inflation bulb is connected to the first port 565, such that the vest inflation bulb can be pumped to inflate the inflatable bladder with air. The coupler can comprise a threaded connection, for example, of the type used to secure an air pump to a tire valve stem. Other couplers can be used, for example, that comprise spring-loaded ball bearings and a grove, such as a coupler used to connect a pressure washer nozzle to a pressure washer spray wand. A second port 544 is located on the left front panel 508. Second port 544 can include a valve that opens into the inflatable bladder of inflatable liner 500. The valve of second port 544 can open when a coupler of an aneroid manometer gauge is connected to the second port 544 such that the aneroid manometer gauge can gauge the gas pressure inside of the inflatable bladder. Inflatable liner 500 can include an opening 548 through the left panel 508 to provide clearance for connecting a cable to an output port of the stethoscope matrix.

FIGS. 5A and 5B illustrate an outside surface 503 of back panel 502, and outside surfaces of right front panel 504 and left front panel 508 of inflatable liner 500. The outside surfaces of the inflatable liner 500 can include a plurality of couplers to releasably connect with the couplers of the outer shell. For example, FIG. 5A shows a second pair of zipper halves 576, 478 including a right liner zipper half 576 stitched to the outside surface along a substantial height of right front panel 504 and a left liner zipper half 578 stitched to the outside surface along a substantial height of left front panel 508. FIG. 5B shows a first lower loop patch 582 and a second lower loop patch 584 stitched to outside surface 503 of back panel 502 adjacent to and above bottom 516. An upper loop patch 580 can be stitched to outside surface 503 of back panel 502 adjacent to and below top 512. First lower loop patch 582, second lower loop patch 584, and upper loop patch 580, can releasably connect to respective hook patches of the outer shell, as described above. Likewise, right liner zipper half 576 and left liner zipper half 578 can be zipped to the respective zipper halves of the outer shell, as described above. Although hook and loop fasteners, and zippers are depicted in particular locations, the same or other fasteners can be used in other locations. Other fasteners can include, but are not limited to, buttons, buckles, ties, snaps, clips, magnetic buttons, clasps, laces, a combination thereof, and the like.

FIG. 5C illustrates an inside surface 501 of back panel 502 of inflatable liner 500. Inside surface 501 includes recesses and channels to fit and retain the stethoscope matrix within. In particular, inside surface 501 of back panel 502 can include a first bell recess 511, a second bell recess 513, a third bell recess 515, and a fourth bell recess 517. Each bell recess 511, 513, 515, 517 is defined by an inner wall 598 shaped to receive a respective bell of the stethoscope matrix and each bell recess 511, 513, 515, 517 includes a retaining lip 595 extending inward from an outer edge of the bell recess 511, 513, 515, 517 to retain a respective stethoscope therein. An inside surface of the left side panel can further include an output port recess 568 to fit and retain an output port within. A first channel 520 can extend from first bell recess 511 to output port recess 568, a second channel 524 can extend from second bell recess 513 to output port recess 568, a third channel 522 can extend from third bell recess 515 to output port recess 568, and a fourth channel 526 can extend from fourth bell recess 517 to output port recess 568. Channels 520, 522, 524, 526 fit and retain respective connectors, for example, pressure tubes, respectively therein.

Figure 5D:
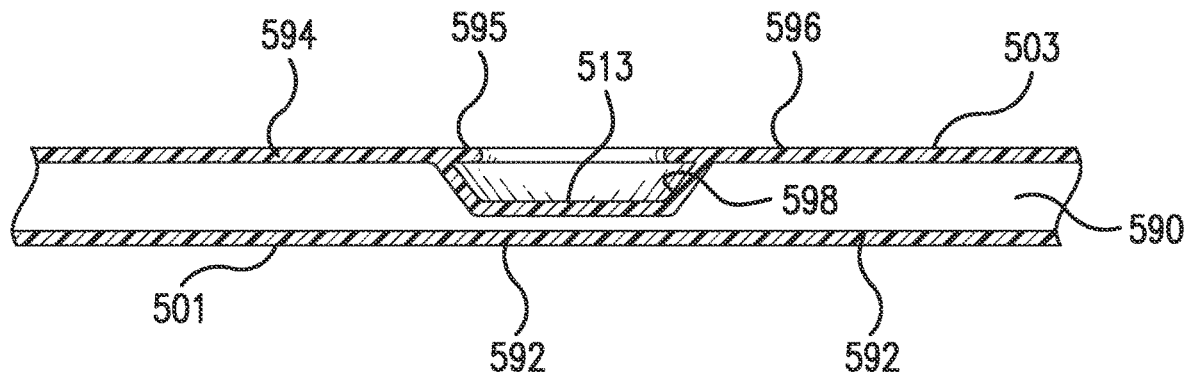
FIG. 5D is a cross-sectional view taken along lines 5D-5D of FIG. 5C and showing the inside of a stethoscope recess.

FIG. 5D is a cross-sectional view taken along line 5D-5D shown in FIG. 5C, illustrating back panel 502 of the inflatable liner and second bell recess 513. Back panel 502 of inflatable liner 500 includes a front wall 594 defining a liner inside surface 503, and a back wall 592 defining an liner outside surface 501. Inflatable bladder 590 is disposed between, and is defined by and comprises, front wall 594 and back wall 592. Second bell recess 513 is defined by inner wall 598 that is recessed into front wall 594.

As mentioned above, retaining lip 595 radially extends from a periphery of inner wall 598, inwardly, toward a center of second bell recess 513. Retaining lip 595 can be made of a flexible and resilient material, such as rubber, silicone, or another flexible polymer material. A bell of a stethoscope can be placed inside second bell recess 513 by stretching and deforming the retaining lip 595 to enlarge the opening to second bell recess 513. Retaining lip 595 is elastically deformable and returns to its original shape after stretching to accommodate a stethoscope bell, to retain the bell within second bell recess 513. Retaining lip 595 can then be stretched and deformed to remove the stethoscope bell from second bell recess 513.

Figure 5E:
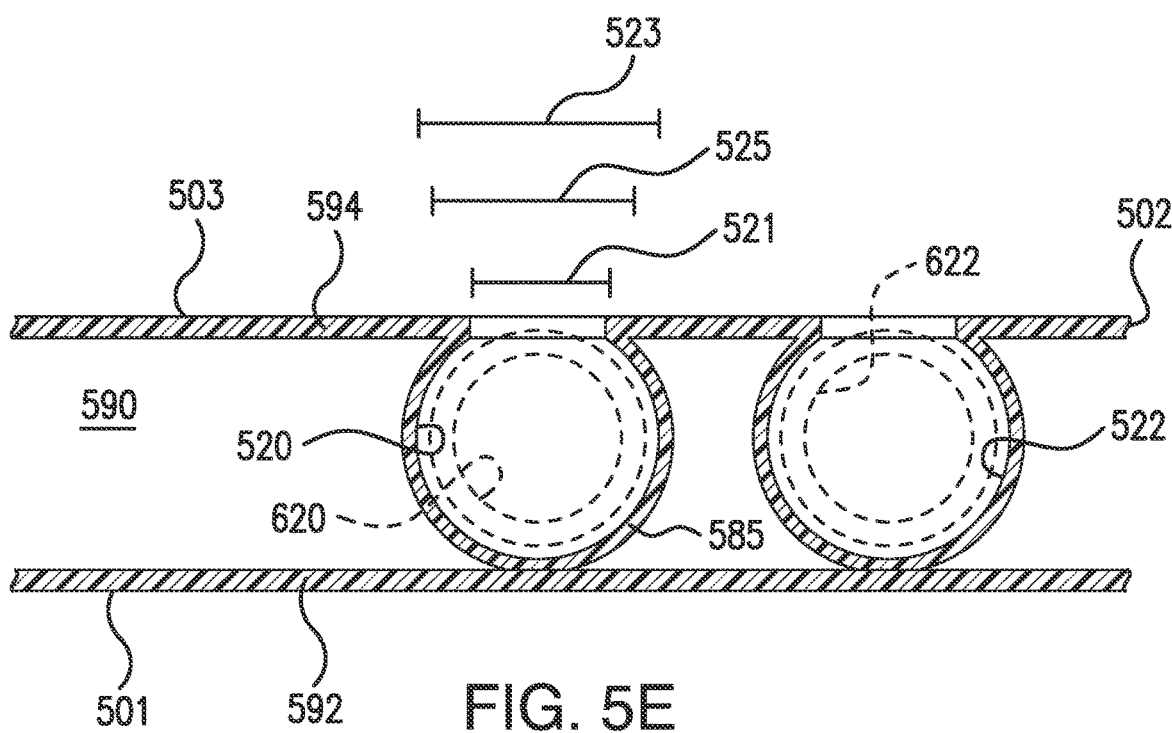
FIG. 5E is a cross-sectional view taken along lines 5E-5E of FIG. 5C and showing a cross-section through two adjacent pressure tube channels, with pressure tubes shown in phantom.

FIG. 5E is a cross-sectional view taken along line 5E-5E of FIG. 5C, illustrating back panel 502 of inflatable liner 500 and showing a section through first channel 520 and third channel 522. Pressure tubes (not present) are shown in phantom. Back panel 502 of inflatable liner 500 includes front wall 594 defining inside liner surface 503, and back wall 592 defining outside liner surface 501. The gas-receiving cavity of inflatable bladder 590 is disposed between front wall 594 and back wall 592. First channel 520 and third channel 522 are defined by an inner wall 585 and each has a tubular shape. Each of first channel 520 and third channel 522 has a longitudinal opening along the length thereof for stretching to receive respective first and third connectors of a stethoscope assembly or matrix. The connectors can comprise or be pressure tubes. For example, first channel 520 and third channel 522 can be configured to stretch and receive respective first connector 620 and third connector 622 of stethoscope matrix 600 shown in FIG. 6A.

Inner wall 585 and front wall 594 can be made of an elastically deformable material, for example, a flexible and resilient material, such as rubber, silicone, or another elastomeric, flexible, and/or polymeric material. As illustrated in FIG. 5E, inner wall 585 of first channel 520 has a diameter 523 that is larger than a diameter 525 of first connector 620, such that first connector 620 can fit inside of first channel 520. The opening of first channel 520 has a width 521 that is smaller than diameter 525 of first connector 620 so that, once the opening to first channel 520 is stretched so that a connector or pressure tube can be inserted into first channel 520, the material defining first channel 520 can elastically rebound such that first connector 620 can be retained within first channel 520.

As mentioned above, front wall 594 and inner wall 585 are made of a flexible and resilient material so that the opening to first channel 520 can be stretched and deformed to expand such that first connector 620 can pass through the opening and fit into first channel 520. The opening then resiliently returns to its original shape so that width 521 is smaller than diameter 525 of first connector 620, thereby retaining first connector 620 inside of first channel 520. To remove first connector 620 from first channel 520, front wall 594 can be stretched and deformed to expand the size of the opening such that first connector 620 can be removed. Stretching and deforming can comprise pulling first connector 620 out of first channel 520.

Figure 6A:
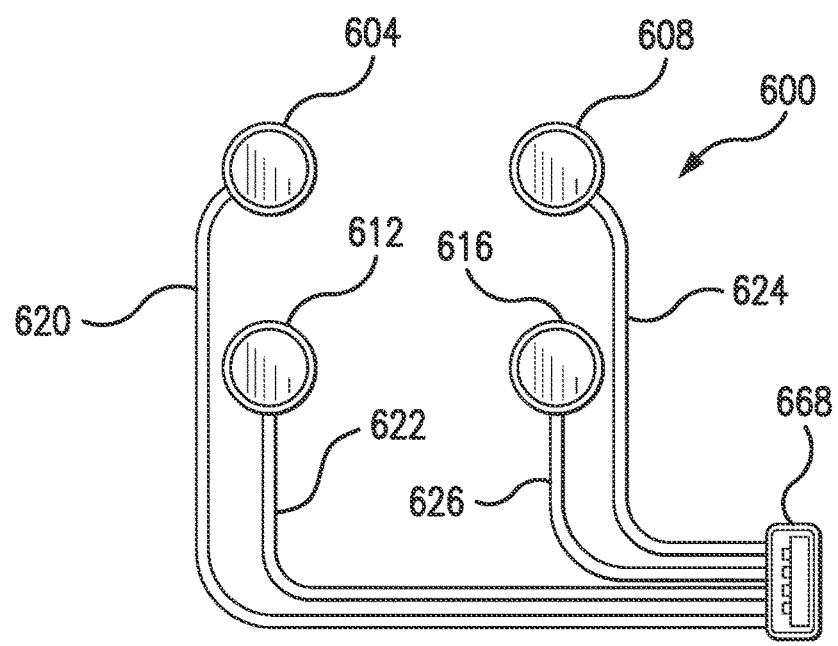
FIG. 6A is a front view of a stethoscope matrix according to various embodiments of the present invention, that can be used with the inflatable liner shown in FIGS. 5A-5E.

FIG. 6A illustrates a stethoscope matrix 600. Stethoscope matrix 600 can include a plurality of stethoscopes connected together. Stethoscope matrix 600 can include one, two, three, four, six, eight, ten, twelve, or more, stethoscopes. The stethoscopes can be arranged in a line, in a circle, in an array, randomly, or the like. Each stethoscope can include a respective bell having a respective flat listening bell surface. As shown, stethoscope matrix 600 comprises four stethoscopes and the four stethoscopes can include a first bell 604, a second bell 608, a third bell 612, and a fourth bell 616. A first connector 620 extends from first bell 604 to an electronic output port 668, a second connector 624 extends from second bell 608 to electronic output port 668, a third connector 622 extends from third bell 612 to electronic output port 668, and a fourth connector 626 extends from fourth bell 616 to electronic output port 668. As mentioned above, electronic output port 668 fits within an output port recess of inflatable liner 500 shown in FIGS. 5A-5E. Connectors 620, 622, 624, 626 fit within respective channels of inflatable liner 500, and bells 604, 608, 612, 616 fit within respective bell recesses of inflatable liner 500. As such, the flat listening bell surfaces can be configured flush with inside surface 503 of back panel 502.

Figure 6B:
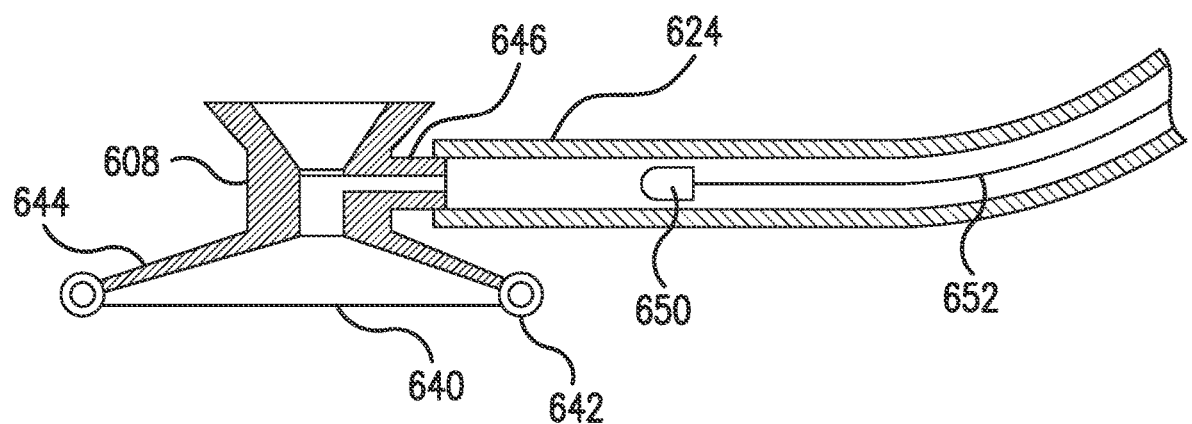
FIG. 6B is an enlarged cross-sectional view through stethoscope 608 shown in FIG. 6A and its associated pressure tube having a microphone positioned therein.

FIG. 6B is a cross-sectional view of second bell 608 and second connector 624 shown in FIG. 6A. Second bell 608 includes a bell body 644 having a bell rim 642 and a bell diaphragm 640. Second bell 608 is connected to second connector 624 at a fitting 646. In this embodiment, second connector 624 is a pneumatic pressure tube that propagates sound waves and pressure waves from second bell 608 toward a microphone 650 within the pneumatic pressure tube. An electrical signal from microphone 650 is communicated via an electrical wire 652 to electronic output port 668 as described in connection with FIG. 6A.

Figure 7:
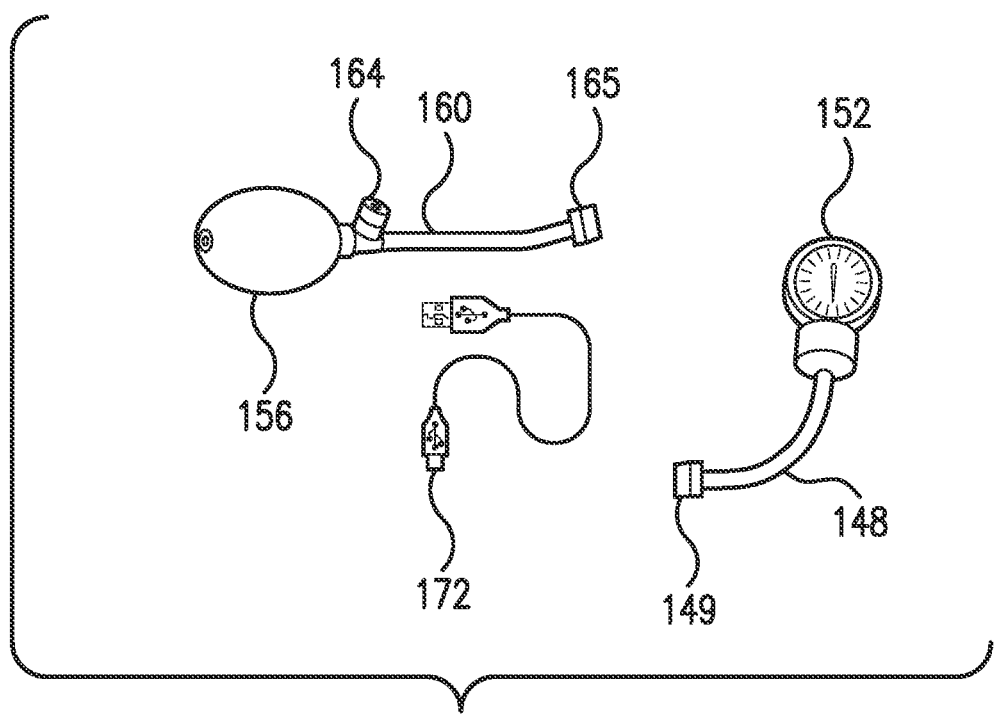
FIG. 7 shows a collection of reusable components that can be used with the modular inflatable vest components shown in FIGS. 4A-6B.

FIG. 7 illustrates various components that are attachable to the modular inflatable vest system shown in FIGS. 4A-6B. A vest inflation bulb 156 can be connected to a port on or in an inflatable vest or inflatable liner by a bulb coupler 165. Vest inflation bulb 156 can be squeezed to pump air through pressure tube 160 to inflate the vest or liner, for example, to inflate one or more inflatable bladders inside a back panel, a right front panel, a left front panel, or a combination thereof, of an inflatable vest or inflatable liner. An air release valve 164 is provided along pressure tube 160 so that an inflatable vest or inflatable liner can be deflated, for example, when not in use, when being stored, or when a patient is putting on the inflatable vest or inflatable liner. Air release valve 164 can include a pressure-release valve or component configured to prevent the inflatable bladder from being overinflated and damaged. A one-way valve or component can be provided downstream of vest inflation bulb 156 so that gas pumped into an inflatable vest or inflatable liner does not immediately flow out of the inflatable vest or inflatable liner.

An aneroid manometer gauge 152 can be connected to a port in or on an inflatable vest or inflatable liner by a gauge coupler 149 connected to pressure tube 148. Aneroid manometer gauge 152 can include an ever-floating needle that constantly shows a pressure reading from within pressure tube 148 and thus from within an inflated vest or inflated liner. Alternatively, aneroid manometer gauge 152 can include a needle system that shows only a maximum pressure measured until the needle position is reset. A digital aneroid manometer gauge can likewise be used.

As also shown in FIG. 7, a USB cable 172 can be used to connect the electronic output port of an inflatable vest or stethoscope matrix for use therewith, to a computing device, for example, to transfer data generated by the stethoscope matrix to a computing device. Other cable types, ports, and connectors can be used, for example, an ethernet cable, a firewire cable, a micro-USB cable, a co-axial cable, an HDMI cable, a video cable, or the like.

The present invention can be used at home or in other locations that are remote from a doctor's office. To use the present invention, a patient can place their arms through arm openings such that the vest surrounds the patient's chest. The patient can then attach the buckles of the straps together or otherwise zip-up or secure the vest to the patient's body. The patient can then pump-up the inflatable bladder of the vest using the bulb pump or another gas pump so that the vest presses against the patient's body and the stethoscopes are pressed against the patient's back, chest, sides, above the shoulders, or against a number of such body parts. The one or more inflatable bladders can be configured to retain air or gas such the stethoscopes are pressed against the patient's body for a desired amount of time. The inflatable vest can be placed directly in contact with a patient's skin or can be used over clothing. The microphones can pick up sound from the user's lungs, heart, cardiopulmonary cavity, peritoneal cavity, or a combination thereof. For example, a heartbeat, heart rate, lung sounds (wheezing, crackling, and the like), excess fluid around the heart and lungs, blood oxygen content, blood pressure, and the like, can be detected using the inflatable vest of the present invention.

Once the sound waves are digitized, for example, by the microphone or by a microphone digital converter, the sound data can be transferred to a computing device via a cable connection or via a wireless connection. For wireless communication, the electronic output port of the inflatable vest can include a wireless communication device, such as a BLUETOOTH module, a WiFi module, or the like. The data can be transferred directly to a doctor, nurse, physician, or clinician, or first transferred to a computing device controlled by the patient, before being sent to a doctor, nurse, physician, or clinician. Data transfer can occur over the Internet, over an intranet, over a phone line, over a satellite connection, over a cable television line, or the like. The data can be sent from the vest directly to a computing device of a remote doctor, nurse, physician, or clinician.

The computing device can process the sound data by mapping the sound data in charts or the like. The computing device can save and present the processed sound data in a structed form such that a doctor can view the sound data and diagnose the patient. Multiple stethoscopes allow different portions of the patient to be monitored and mapped, for example, individually, together, or in any combination.

In certain embodiments of the present invention, a system is provided whereby the sound data can be stored and compared with past or future sound data. For example, a patient can use the inflatable vest of the present invention to obtain first data on a first day. The first data can be sent to a computing device of a remote doctor to be processed. The patient can then use the inflatable vest to obtain second data on of a second day, which can again be sent to the computing device of the remote doctor to be processed. The second data can be processed with and compared with the first data. This method can continue over days, weeks, months, or years, such that data of the patient is continuously compiled and compared to monitor changes in a patient's condition. Trends can be determined and compared with treatments, for example, hemodialysis treatment schedules and parameters. The respiratory assessments can then be used to optimize the patient's health and well-being and to make adjustments to treatments and treatment schedules.

The entire contents of all references cited in this disclosure are incorporated herein in their entireties, by reference. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether such a range is separately disclosed. Where a range of numerical values is recited herein, unless otherwise stated, the range is intended to include the endpoints thereof, and all integers and fractions within the range. It is not intended that the scope of the invention be limited to the specific values recited when defining a range.

All patents, patent applications, and publications mentioned herein are incorporated herein in their entireties, by reference, unless indicated otherwise.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. An inflatable vest for respiratory assessment, the inflatable vest comprising:
   a vest garment configured to be worn on a torso of a patient, the vest garment comprising an outer shell having an inside surface, an inflatable liner defining an inflatable bladder and having an outside surface and an inside surface, and a coupler, wherein the inside surface of the inflatable liner defines a plurality of stethoscope recesses, the outside surface of the inflatable liner is removably attached to the inside surface of the outer shell by the coupler, and the inside surface of the inflatable liner is configured to press against the back of a patient;
   a matrix of stethoscopes comprising at least a first stethoscope and a second stethoscope, each stethoscope of the matrix of stethoscopes comprising a bell, a diaphragm across the bell, and a pressure tube extending away from the bell, each stethoscope of the matrix of stethoscopes being sized such that the bell fits within one respective stethoscope recess of the plurality of stethoscope recesses in a manner such that the respective diaphragm is flush with the inside surface of the inflatable liner, the matrix of stethoscopes further comprising a manifold tube connected to the pressure tube of the first stethoscope and the pressure tube of the second stethoscope, the matrix of stethoscopes being removably attached to the inflatable liner; and
   a matrix of microphones including respective microphones positioned within respective pressure tubes of the respective stethoscopes of the matrix of stethoscopes, wherein
   the inflatable vest is configured such that, when the matrix of stethoscopes is recessed into the plurality of stethoscope recesses, and the inflatable vest is worn by a patient, and the inflatable bladder is inflated, the diaphragms of the matrix of stethoscopes are pressed against the back of the patient,
   the plurality of stethoscope recesses comprises a plurality of bell recesses and a plurality of pressure tube channels, and
   each of the plurality of bell recesses comprises an inner wall defining a bell shape, and a lip radially extending inwardly from a periphery of the inner wall, the lip comprising an elastically deformable material.

2. The inflatable vest of claim 1, wherein the stethoscope matrix further comprises an electronic output port connected to the matrix of stethoscopes, by the manifold tube.

3. The inflatable vest of claim 2, wherein the electronic output port comprises a cable port, a wireless transmitter, or a combination thereof, and is configured to transmit data captured by the matrix of microphones, to a computing system.

4. The inflatable vest of claim 2, wherein the inside surface of the inflatable liner further comprises an electronic output port recess that receives and retains the output port therein.

5. The inflatable vest of claim 1, wherein each of the pressure tube channels comprises an inner wall defining a tubular shape having an opening along a length thereof to receive a respective pressure tube therein.

6. The inflatable vest of claim 5, wherein the inner wall comprises an elastically deformable material.

7. An inflatable vest for respiratory assessment, the inflatable vest comprising:
   a vest garment configured to be worn on a torso of a patient, the vest garment comprising an outer shell having an outside surface and an inside surface, an inflatable liner defining an inflatable bladder and having an outside surface and an inside surface, and a coupler, wherein the inside surface of the inflatable liner defines a plurality of stethoscope recesses, the outside surface of the inflatable liner is removably attached to the inside surface of the outer shell by the coupler, the inside surface of the inflatable liner is configured to press against the back of a patient, and each stethoscope recess of the plurality of stethoscope recesses comprises a bell recess and a pressure tube channel;
   a matrix of stethoscopes, the matrix of stethoscopes being releasably attached to the inside surface of the inflatable liner, each stethoscope of the matrix of stethoscopes comprising a bell, a diaphragm across the bell, and a pressure tube extending away from the bell, each stethoscope of the matrix of stethoscopes being sized such that the respective bell fits within one respective stethoscope recess of the plurality of stethoscope recesses in a manner such that the respective diaphragm is flush with the inside surface of the inflatable liner, and each pressure tube having a diameter; and
   a matrix of microphones including respective microphones positioned within respective pressure tubes of respective stethoscopes of the matrix of stethoscopes, wherein
   the inflatable vest is configured such that, when a respective stethoscope of the matrix of stethoscopes is recessed into a respective stethoscope recess of the plurality of stethoscope recesses, and the inflatable vest is worn by a patient, and the inflatable bladder is inflated, the diaphragm of the respective stethoscope is pressed against the back of the patient,
   each pressure tube channel comprises an inner wall defining a tubular shape having an opening along a length thereof and is configured to receive a respective pressure tube therein, and
   each opening has a width that is less than the diameter of the respective pressure tube.

8. The inflatable vest of claim 7, wherein the coupler comprises a first pair of zipper halves attached to the inside surface of the outer shell and a second pair of zipper halves attached to the outside surface of the inflatable liner, wherein the first pair of zipper halves are zipped to the second pair of zipper halves.

9. The inflatable vest of claim 7, wherein the coupler comprises one or more of hook patches and loop patches attached to the outside surface of the inflatable liner, and one or more of hook patches and loop patches attached to the inside surface of the outer shell.

10. The inflatable vest of claim 7, wherein the inflatable liner comprises an inflation port connected to the inflatable bladder, and a pressure port connected to the inflatable bladder.

11. The inflatable vest of claim 10, further comprising a vest inflation bulb comprising a bulb coupler, wherein the bulb coupler is releasably attached to the inflation port.

12. The inflatable vest of claim 10, further comprising an aneroid manometer gauge comprising a gauge coupler, wherein the gauge coupler is releasably attached to the pressure port.

13. A method of assembling the inflatable vest of claim 7, comprising:
   coupling the inflatable liner to the outer shell, using the coupler; and
   positioning the matrix of stethoscopes in the plurality of stethoscope recesses.

14. A method of making a respiratory assessment of a patient, comprising:
   placing the inflatable vest, of claim 7, on a patient;
   inflating the inflatable bladder to press the matrix of stethoscopes against the back of the patient; and
   transmitting respiratory signals generated by the matrix of stethoscopes from the inflatable vest to a receiver that is remote from the inflatable vest.

15. The method of claim 14, wherein the inflatable vest further comprises a heart rate monitor and a pulse oximeter, and the method further comprises transmitting heart rate signals and blood oxygen signals from the inflatable vest to a receiver that is remote from the inflatable vest.

* * * * *